(12) United States Patent
Muffoletto et al.

(10) Patent No.: US 11,696,769 B2
(45) Date of Patent: Jul. 11, 2023

(54) THERMALLY SENSITIVE RETENTION MECHANISM FOR ORTHOPEDIC CUTTING INSTRUMENTS

(71) Applicant: VIANT AS&O HOLDINGS, LLC, Foxborough, MA (US)

(72) Inventors: Mark T. Muffoletto, Darien Center, NY (US); Kari T. Anastasia, Buffalo, NY (US)

(73) Assignee: VIANT AS&O HOLDINGS, LLC, Foxborough, MA (US)

( * ) Notice: Subject to any disclaimer, the term of this patent is extended or adjusted under 35 U.S.C. 154(b) by 126 days.

(21) Appl. No.: 16/230,520

(22) Filed: Dec. 21, 2018

(65) Prior Publication Data
US 2019/0192171 A1 Jun. 27, 2019

Related U.S. Application Data

(60) Provisional application No. 62/609,469, filed on Dec. 22, 2017.

(51) Int. Cl.
| | |
|---|---|
| A61B 17/16 | (2006.01) |
| B25B 23/00 | (2006.01) |
| A61B 1/00 | (2006.01) |
| A61B 17/00 | (2006.01) |
| A61B 90/00 | (2016.01) |

(52) U.S. Cl.
CPC .......... *A61B 17/1617* (2013.01); *A61B 17/16* (2013.01); *B25B 23/00* (2013.01); *A61B 1/00103* (2013.01); *A61B 17/1666* (2013.01); *A61B 17/1677* (2013.01); *A61B 2017/0023* (2013.01); *A61B 2017/0046* (2013.01); *A61B 2017/00473* (2013.01); *A61B 2017/00955* (2013.01); *A61B 2090/0814* (2016.02)

(58) Field of Classification Search
CPC ............ A61B 17/1666; A61B 17/1677; A61B 2017/0023; A61B 1/00103; A61B 2090/0814
See application file for complete search history.

(56) References Cited

U.S. PATENT DOCUMENTS

| | | | | |
|---|---|---|---|---|
| 4,456,010 A | * | 6/1984 | Reimels | A61B 17/1695 408/139 |
| 4,951,690 A | * | 8/1990 | Baker | A61B 17/1695 128/898 |
| 5,295,992 A | * | 3/1994 | Cameron | A61B 17/1677 407/54 |

(Continued)

FOREIGN PATENT DOCUMENTS

WO 9837819 A1 9/1998

OTHER PUBLICATIONS

International Search Report dated Apr. 1, 2019 relating to corresponding application PCT/US2018/67446.

*Primary Examiner* — Matthew J Lawson
(74) *Attorney, Agent, or Firm* — Grossman, Tucker, Perreault & Pfleger, PLLC

(57) ABSTRACT

The present invention is directed at a thermally sensitive retention mechanism for orthopedic cutting instruments. More specifically, the present invention incorporates structural engagement features into a rotational orthopedic cutting instrument that transfers torque from a driver to a cutting component and which upon heating result in disengagement of the cutting component from the driver portion.

12 Claims, 4 Drawing Sheets

(56) References Cited

U.S. PATENT DOCUMENTS

| | | | |
|---|---|---|---|
| 5,569,163 | A | 10/1996 | Francis et al. |
| 5,779,686 | A | 7/1998 | Sato et al. |
| 6,869,392 | B2 | 3/2005 | Dickopp et al. |
| 8,382,804 | B2 | 2/2013 | Thomke et al. |
| 11,517,296 | B2* | 12/2022 | Kratoska ............... A61B 17/29 |
| 2002/0165549 | A1* | 11/2002 | Owusu-Akyaw ......................... A61B 17/1628 606/80 |
| 2006/0111725 | A1* | 5/2006 | Biegun ............. A61B 17/1659 606/85 |
| 2008/0167653 | A1* | 7/2008 | Watlington ........ A61B 17/1688 606/81 |
| 2008/0215053 | A1 | 9/2008 | Thomke et al. |
| 2009/0065565 | A1 | 3/2009 | Cao |
| 2011/0202060 | A1* | 8/2011 | White ................ A61B 17/1666 606/80 |
| 2012/0191099 | A1* | 7/2012 | Victor ................ A61B 17/1666 606/81 |
| 2013/0053852 | A1* | 2/2013 | Greenhalgh ....... A61B 17/1659 606/83 |
| 2015/0066030 | A1* | 3/2015 | McGinley ......... A61B 17/1628 606/79 |
| 2016/0089158 | A1* | 3/2016 | Fortin ................ A61B 17/1615 606/81 |
| 2017/0007852 | A1* | 1/2017 | Isola ............. A61B 17/320068 |
| 2017/0181756 | A1 | 6/2017 | Slone et al. |
| 2017/0231643 | A1* | 8/2017 | Victor ................ A61B 17/1659 606/80 |
| 2018/0085100 | A1 | 3/2018 | Kratoska |
| 2023/0000582 | A1* | 1/2023 | Bailey ................... A61B 90/08 |

* cited by examiner

THERMALLY SENSITIVE RETENTION MECHANISM FOR ORTHOPEDIC CUTTING INSTRUMENTS

CROSS-REFERENCE TO RELATED APPLICATIONS

This application claims the benefit of U.S. Provisional Application 62/609,469 filed Dec. 22, 2017 which is fully incorporated herein by reference.

FIELD

The present invention is directed at a thermally sensitive retention mechanism for orthopedic cutting instruments. More specifically, the present invention incorporates structural engagement features into a rotational orthopedic cutting instrument that transfers torque from a driver to a cutting component and which upon heating result in disengagement of the cutting component from the driver portion.

BACKGROUND

There have been a variety of reported efforts to provide a disposable medical device with a design that prevents the medical device from being utilized a second time. For example, U.S. Pat. No. 5,569,163 entitled Disposable Surgical Instrument discloses the use of a lens mounting element molded from a material such as a natural or synthetic polymer which is capable of deforming in the presence of a deforming agent such as water, organic solvent, heat, gas, or light. U.S. Pat. No. 5,779,686 is entitled Disposable Medical Instrument and discloses a medical instrument which cannot be reused if it is washed after use, or which makes it possible to judge whether the medical instrument has been washed thereby precluding reuse. U.S. Pat. No. 6,869,392 is entitled Disposable Implement Inserted Into An Endoscope and discloses the use of a disposable implement insertable into an endoscope and comprising at least one zone matched to the shape of the endoscope that is designed to be permanently deformed on account of having been used a first time by the inevitable mechanical, thermal and/or chemical treatment it undergoes in the endoscope. U.S. Pat. No. 8,382,804 is entitled Prevention Of Reuse Of A Medical Device and discloses the use of a clamp that has an element that alters its appearance while being heated over a threshold temperature, thus giving optical or mechanical information that the device should not be used a second time. U.S. Publ. No. 2009/0065565 is entitled System, Method And Apparatus For Preventing Reuse Of Medical Instruments and discloses a circuit embedded in the disposable medical device to identify the device and a circuit for reading the status, such as whether the device has been used. WO98/37819 is entitled Preventing Reuse Of Surgical Devices and discloses a single use ultrasonic surgical device that relies upon the use of a hub coupled to the transmission component and includes a temperature sensitive material that distorts when exposed to heat.

Accordingly, there exists a continuing need for surgical instrument designs that will prevent re-use of the instrument, and in particular, re-use of orthopedic cutting instruments, which would then reduce the problems associated with cleanliness and sterility of patients undergoing orthopedic procedures in which articular surfaces are removed, resurfaced and prepared to receive an implant.

SUMMARY

A cutting instrument comprising a driver component adapted to provide a rotating torque motion including an end portion containing one or a plurality of axial-bearing bosses and optionally one or a plurality of torque-bearing bosses and a cutting component including one or a plurality of holes to engage with said axial bearing bosses and said optional torque-bearing bosses. The axial-bearing bosses comprise a temperature sensitive material which upon exposure to steam sterilization do not allow for engagement of said axial-bearing bosses with said cutting component to thereby prevent reuse of the cutting instrument.

In related embodiment the present invention relates to a cutting instrument comprising: a driver component adapted to provide a rotating torque motion including an end portion containing: (i) one or a plurality of axial-bearing bosses having a height in the range of 1.0 mm to 4.0 mm and a diameter of 0.25 mm to 4.0 mm, and (ii) one or a plurality of torque-bearing bosses having a height in the range of 1.0 mm to 4.0 mm and a diameter of 0.25 mm to 4.0 mm. The cutting instrument also includes a cutting component including one or a plurality of holes to engage with said axial bearing bosses and said optional torque-bearing bosses. The axial-bearing bosses comprise a temperature sensitive material which upon exposure to steam sterilization do not allow for engagement of said axial-bearing bosses with said cutting component to thereby prevent reuse of the cutting instrument.

In method form, the present invention relates to a method for preventing reuse of an orthopedic cutting instrument comprising: providing a driver component adapted to provide a rotating torque motion including an end portion containing one or a plurality of axial-bearing bosses and optionally one or a plurality of torque-bearing bosses. One then provides a cutting component including one or a plurality of holes to engage with said axial bearing bosses and said optional torque-bearing bosses. This is followed by engaging said axial-bearing bosses to said cutting component wherein said axial-bearing bosses comprise a temperature sensitive material which upon exposure to steam sterilization disengage from said cutting component to thereby prevent reuse of the cutting instrument.

BRIEF DESCRIPTION OF THE DRAWINGS

The invention can be best understood by reference to the following detailed description of the preferred embodiments when considered in conjunction with the accompany drawings wherein.

DETAILED DESCRIPTION OF PREFERRED EMBODIMENTS

Figure 1:
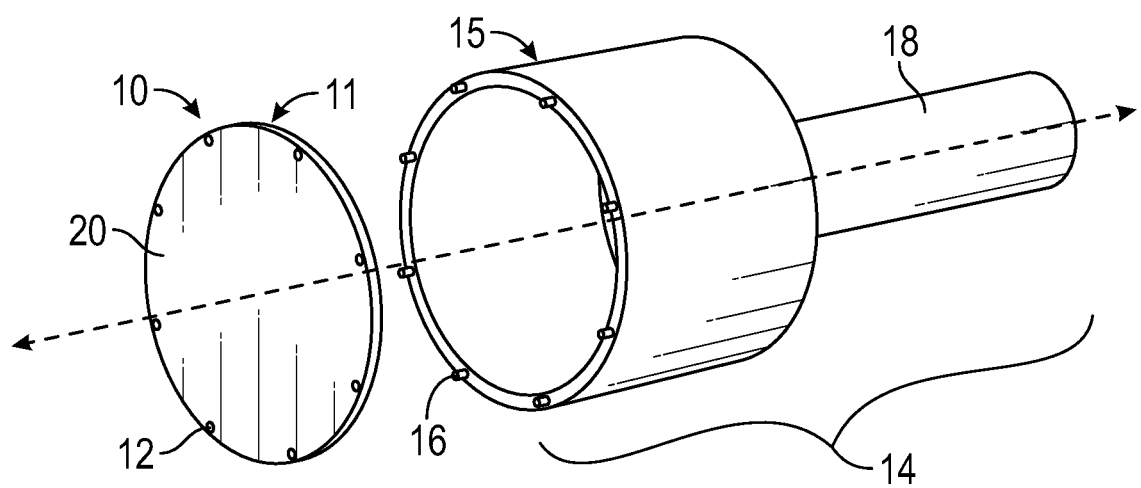
FIG. 1 illustrates an example of the present invention in the form of an unassembled patella reaming instrument.

With attention directed to FIG. 1, the present invention is illustrated in the form of an unassembled patella reaming instrument having a cutting component 10 that has the indicated holes 12 preferably along the perimeter 11 of the component. Preferably, the holes are positioned such that they are within 1-10 mm of the perimeter 11. Also shown is driver interface component 14 which has standing bosses 16. The standing bosses are positioned on an end portion 15 such that they will align with the holes 12 on the cutting component 10. The driver interface component is adapted to provide a rotating torque motion to the cutting component 10. For clarity, the cutting edges are not shown on the cutting component. Reference to a standing boss 16 may be understood as a protruding feature from a surface of the driver that is intended to be located in the corresponding holes 12. In the broad context of the present invention the total number of standing bosses may preferably fall in the range of 1-10, with a height preferably in the range of 1.0 mm to 4.0 mm, more preferably 2.0 mm to 3.0 mm, and most preferably, a height of 2.5 mm with a +/−0.1 mm tolerance. The standing bosses also may be of any geometrical shape, but are preferably round or oval. The standing bosses preferably have a diameter of 0.25 mm to 4.0 mm, most preferably 1.5 mm to 3.5 mm, and in an even more preferred embodiment, a diameter of 2.0 mm at a +/−0.1 mm tolerance.

The standing bosses are preferably of two types and formed from two different materials. That is, a first material which defines the bosses as torque-bearing bosses and a second material that defines the bosses as axial-bearing bosses. The torque bearing bosses are preferably made to protrude and releasably engage through holes 12 and are capable of transferring torque from the driver interface 14 to the cutting component 10. It should be noted that the torque-bearing bosses are optional, in the sense that it is contemplated herein that the only bosses necessary are the axial-bearing bosses, further described herein. However, to the extent that torque-bearing bosses are utilized, they are preferably present at a level of 1 torque-bearing boss to a plurality of torque bearing bosses, more preferably up to and including 9 torque-bearing bosses. The corresponding number of axial-bearing bosses are preferably present at a minimum level of 1 axial-bearing boss to a plurality of axial bearing bosses, more preferably up to 9 axial bearing bosses. This in turn provide that the total number of bosses, as noted above, is preferably in the range of 1-10 bosses.

The torque-bearing bosses that are releasably engaged in through-holes 12 are preferably made of material that does not soften during steam sterilization, as described herein. Accordingly, the torque-bearing bosses are such that they preferably maintain their torque-bearing ability following steam sterilization. Preferred materials for the torque-bearing bosses include both polymeric material and/or metallic material. Polymer material preferably includes polysulfones, such as polyphenylsulfone sold under the tradename Radel® R-5100, available from Solvay. In addition the torque-bearing bosses may be made from a polyarylamide sold under the tradename Ixef® HC-1022 also available from Solvay.

The axial-bearing bosses are to be understood as mechanical engaging with the driver and which serve to releasable secure the driver to the cutting component. More specifically, the axial-bearing bosses secure the cutting component to the driver and reduce or prevent movement along the axial or longitudinal axis 18 during a given cutting procedure. Preferably, when the cutting component is assembled to the driver, the axial-bearing bosses are heat-staked such that the boss material melts flush to the surface 20 of the cutting component or below the cutting surface. Heat staking is reference to the general procedure where the bosses 16 are positioned in holes 12 and the bosses are then deformed with heating which mechanical engages the driver 14 to the cutting component 10. Other contemplated procedures for engaging the axial-bearing bosses to the driver include exposure of the bosses to ultrasonic welding or swaging. Swaging is reference to cold-forming of the axial-bearing boss to the cutting component such that the axial bearing boss is again flush to the surface of the cutting component after joining.

Figure 2:
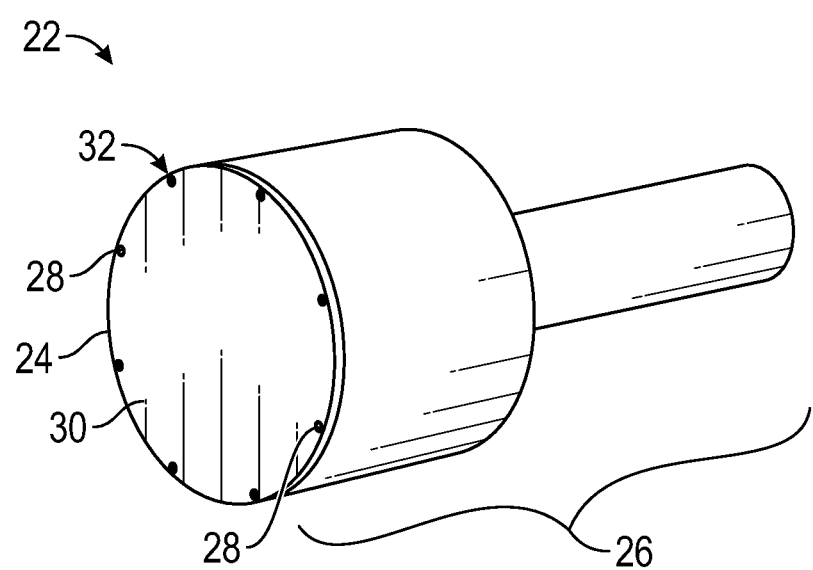
FIG. 2 illustrates the assembled configuration of the patella reamer illustrated in FIG. 1.

Attention is directed to FIG. 2 which illustrates the assembled configuration of the patella reamer illustrated in FIG. 1 therein providing a cutting instrument 22 having a cutting component 24 and a driver component 26. As can be seen, after heat-staking, the two axial-bearing bosses 28 (white) which are directly opposed to one another on the circular cutting component 24, are flush to the surface 30 of the cutting component 24 after the heat staking procedure. Meanwhile, the six torque bearing bosses 32 (black) are originally designed to be flush to the cutting surface 30. Accordingly, in this particular preferred example, there are two axial bearing bosses heat-staked to the cutting component, six torque-bearing bosses that are releasably engaged to cutting component 24, and the total number of bosses is eight. It should be appreciated that while the torque-bearing bosses 32 are present to transfer torque from the driver component 26 to the cutting component 24, the axial-bearing bosses also serve to transfer torque, but since they preferably made from a relatively lower melting material than the torque-bearing bosses, with a relatively lower flexural modulus, their ability to transfer torque is not as efficient as the torque-bearing bosses.

The axial-bearing bosses are therefore preferably made from a temperature sensitive material that will soften and flow during a steam-sterilization protocol such that they no longer remain engaged to the cutting component to prevent reuse of the cutting instrument. Or, stated another way, the axial-bearing bosses are such that upon exposure to steam-sterilization, they convert to a form that will not allow for engagement of the driver component 26 to the cutting component 24. This in turn will provide that the cutting instrument will not be reused and will be limited to a single use since after steam sterilization, the instrument will not function for a selected cutting procedure as the cutting component 24 will not be secured to the driver 26. Accordingly, the axial-bearing bosses herein, which as noted soften and flow during steam sterilization, may be understood as providing a reuse inhibiting feature since after steam sterilization, such bosses will no longer engage with the cutting component and assume any axial load and will render the instrument inoperable. This in turn will eliminate the risks to patients of having a dull and potentially unsanitary cutting instrument otherwise suitable for an orthopedic procedure. Stated another way, the surgeon will now receive a cutting instrument herein in a clean and sterile form limited to a one-time use. The surgeon is assured that such instrument will therefore be sharp and suitable for resurfacing of bone material. Once the surgery is complete, the process utilized by hospitals to clean and sterilize the instrument (i.e. steam sterilization) will, as noted, render the instrument unworkable and prevent the surgeon from using the instrument on a second patient.

The steam sterilization protocol herein is one in which the device will be exposed to steam and temperatures of preferably 121° C. to 134° C. for a time of 3 minutes to 15 minutes, that is best accomplished in an autoclave. Preferably, the axial-bearing bosses are made from a polymeric material that indicates a melting temperature (Tm) of less than 121° C., or in the range of 60° C. to less than 121° C. Such polymeric material is also one that preferably indicates a melt flow index (MFI) in the range of 5-500, more preferably 25-500. Melt flow index is conveniently determined according to ISO standard 1133-1 (Dec. 1, 2011). Accordingly, upon exposure to such steam-sterilization, as noted above, the axial-bearing bosses will soften as flow. However, it is useful to note that both the axial-bearing bosses and torque-bearing bosses herein are such that they may both be capable of undergoing alternative sterilization procedures prior to initial use of the cutting instruments herein. This would include, but is not limited to sterilization by exposure to gamma radiation or ethylene oxide (ETO) sterilization protocols.

Preferably, the axial-bearing bosses are sourced from polycarprolactone, which is available under the trade name CAPA™ and identified as a thermoplastic material available from Perstorp with a reported melting point of around 60° C. The axial-bearing bosses may also be preferably made from an ethylene-co-vinyl-acetate polymer, under the trade name ELVAX™ available from DuPont, with a reported melting point of around 87° C. More specifically, ELVAX™ 250 with a melt flow index of 25, ELVAX™ 410 with a melt flow index of 500 and ELVAX 420 with a melt flow index of 150.

Figure 3:
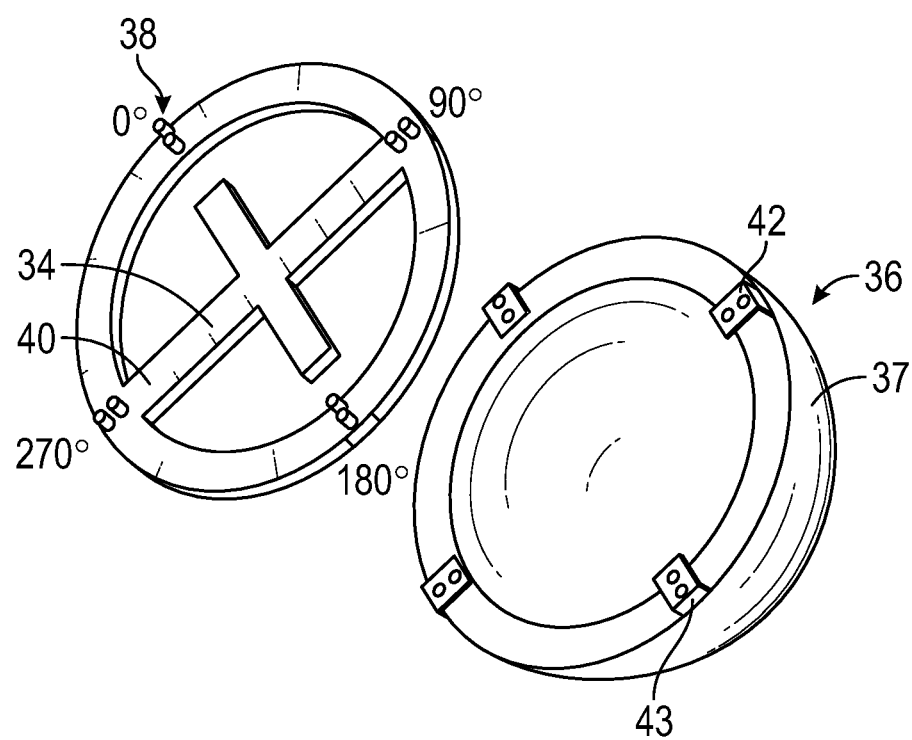
FIG. 3 illustrates another example of the present invention in the form of an unassembled acetabular reaming instrument.

Attention is next directed to FIG. 3, which illustrates another example of a cutting instrument in the context of the present invention. More specifically, FIG. 3 identifies an unassembled acetabular reaming instrument having a driver assembly 34 and a cutting component 36. The cutting component may have a hemispherical type cutting surface 37. Again, for clarity, the cutting edges are not shown on the cutting component. The driver again is configured to have standing bosses 38 that extend from the surface 40 of the driver and are designed to be located in corresponding holes 42 on the cutting component 36. In addition, as can be seen, the holes on the cutting component are provided in the form of tab 43 that may be attached to the cutting component 36 or such tabs may be part of and extend directly from the cutting component 36.

Figure 4:
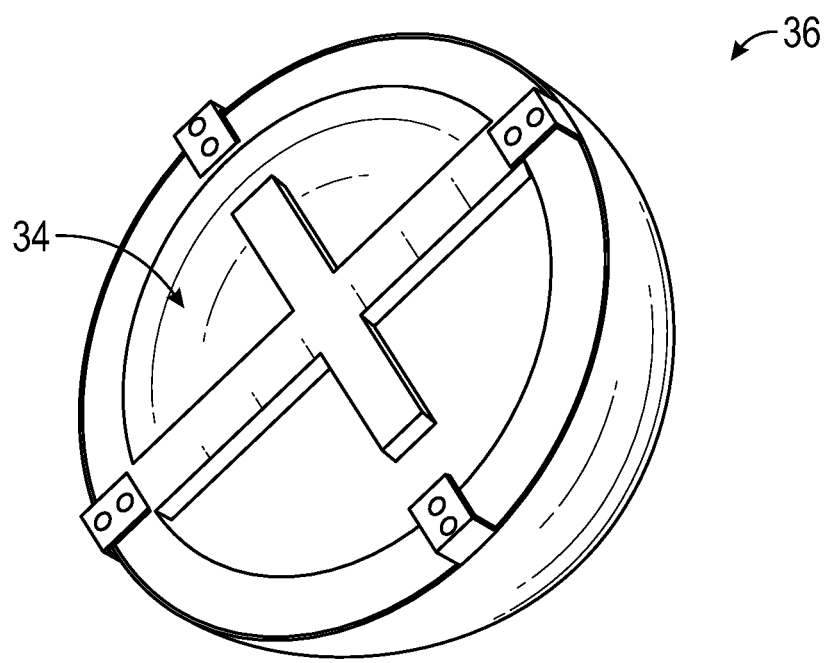
FIG. 4, illustrates the assembly of the unassembled acetabular reaming instrument shown in FIG. 3.

As can be seen in this exemplary embodiment, the standing bosses 38, which may all be axial-bearing bosses, are shown as a pair of standing bosses located at what may be described as the 0°, 90°, 180° and 270° location about the circular perimeter of the driver assembly 34. It should therefore be appreciated that in the broad context of the present invention, with respect to a driver having a generally circular configuration, the bosses may be preferably disposed as such relative angular locations, or at only the 0° and 180° location, or only at the 90° and 270° location. Alternatively, if three (3) the bosses herein are utilized, such bosses may be placed at the 0°, 120° and 240° locations. Finally, attention is directed to FIG. 4, which illustrates the assembly of the unassembled acetabular reaming instrument shown in FIG. 3 wherein the driver assembly 34 and a cutting component 36 are jointed and the axial-bearing bosses have been heat-staked to the cutting component. Although not shown, one or more of the axial-bearing bosses may be replaced with a torque-bearing boss.

With regards to the standing bosses herein, it should be noted that the use of the axial-bearing bosses alone, or in combination with the torque-bearing bosses, are such that they preferably provide the ability to support a torque load, as between the driver and the rotational cutting surface, in the range of 1 Nm to 40 Nm, more preferably in the range of 5 Nm to 20 Nm. In addition, it should now be appreciated that the use of the coupling system herein that relies upon the axial-bearing bosses, either alone or in combination with the torque-bearing bosses, may be used to couple a driver providing a rotary motion to a rotatory cutting component, in an orthopedic reamer, such as in the above exemplary patella reamer design or acetabular reaming instrument. However, in the broad context of the present invention, such bosses may be utilized in glenoid reamers, intramedullary reamers or calcar reamers.

What is claimed is:

1. A method for preventing reuse of an orthopedic cutting instrument comprising:
   providing an orthopedic cutting instrument comprising a driver component and a cutting component;
   wherein:
      the cutting component comprises a plurality of holes;
      the driver component is adapted to provide a rotating torque motion and comprises an end portion comprising at least one axial bearing boss and at least one torque bearing boss, said torque bearing boss releasably engaged to at least one of said cutting component plurality of holes and does not soften during steam sterilization;
      the at least one axial bearing boss is engaged within at least one of the plurality of holes of the cutting component to couple the driver component to the cutting component; and
      the at least one axial bearing boss comprises a temperature sensitive material such that when said cutting instrument is exposed to steam sterilization, the at least one axial bearing boss disengages from the at least one of the plurality of holes of the cutting component and converts to a form that will not allow engagement of said driver component to said cutting component thereby preventing reuse of the cutting instrument; and wherein said cutting component has a perimeter and at least one hole in said plurality of holes in said cutting component is positioned either along or within 1-10 mm of said cutting component perimeter.

2. The method of claim 1, wherein:
   said at least one axial bearing boss comprises a plurality of axial bearing bosses;
   said at least one hole comprises at plurality of holes; and
   each of said plurality of axial bearing bosses is engaged within a respective one of said plurality of holes.

3. The method of claim 1 wherein said at least one axial bearing boss has a height in the range of 1.0 mm to 4.0 mm and a diameter of 0.25 mm to 4.0 mm.

4. The method of claim 1 wherein said temperature sensitive material is a polymeric material having a melt flow index of 5-500.

5. The method of claim 1 wherein said at least one axial bearing boss has a melting temperature of less than 121° C.

6. The method of claim 1 wherein said temperature sensitive material is a polymeric material with melting point in the range of 60° C. to less than 121° C.

7. The method of claim 1 wherein said driver component is configured to provide a rotating torque motion to said cutting component at a torque load of 1 Nm to 40 Nm.

8. The method of claim 1 wherein said cutting instrument comprises a patella reamer, an acetabular reaming instrument, a glenoid reamer, an intramedullary reamer or a calcar reamer.

9. The method of claim 1 wherein said temperature sensitive material is a polycaprolactone or an ethylene-vinyl-co-acetate.

10. The method of claim 1 wherein said torque-bearing boss is a polysulfone or a polyacrylamide.

11. The method of claim 1 wherein the at least one axial bearing boss is heat-staked to said cutting component and said at least one torque bearing boss is releasably engaged to said cutting component.

12. A method for preventing reuse of an orthopedic cutting instrument comprising:
providing an orthopedic cutting instrument comprising a driver component and a cutting component;
wherein:
the cutting component comprises a plurality of holes;
the driver component is adapted to provide a rotating torque motion and comprises an end portion comprising at least one axial bearing boss and at least one torque bearing boss, said torque bearing boss releasably engaged to at least one of said cutting component plurality of holes and does not soften during steam sterilization;
the at least one axial bearing boss is engaged within at least one of the plurality of holes of the cutting component to couple the driver component to the cutting component; and
the at least one axial bearing boss comprises a temperature sensitive material such that when said cutting instrument is exposed to steam sterilization, the at least one axial bearing boss disengages from the at least one of the plurality of holes of the cutting component and converts to a form that will not allow engagement of said driver component to said cutting component thereby preventing reuse of the cutting instrument.

* * * * *